United States Patent
Price

[19]

[11] Patent Number: 6,143,195
[45] Date of Patent: *Nov. 7, 2000

[54] TREATMENT OF ACID GENERATING SULFIDE BEARING MATERIAL

[76] Inventor: Charles Theodore Price, 3300 Hillpoint Dr., Charleston, W. Va. 29302

[*] Notice: This patent issued on a continued prosecution application filed under 37 CFR 1.53(d), and is subject to the twenty year patent term provisions of 35 U.S.C. 154(a)(2).

[21] Appl. No.: 09/071,325

[22] Filed: May 1, 1998

Related U.S. Application Data

[62] Division of application No. 08/678,233, Jul. 11, 1996, Pat. No. 5,846,279.

[51] Int. Cl.$^7$ ........................................................ C02F 1/72
[52] U.S. Cl. ..................................... 252/186.1; 252/186.21
[58] Field of Search ........................ 252/1, 89.1, 186.1, 252/186.21; 405/128; 510/405

[56] References Cited

U.S. PATENT DOCUMENTS

| | | | |
|---|---|---|---|
| 4,018,679 | 4/1977 | Bölsing | 210/925 |
| 4,756,846 | 7/1988 | Matsuura et al. | 252/156 |
| 5,645,821 | 7/1997 | Libin | 424/49 |

OTHER PUBLICATIONS

Rich, Douglas H., "Lime Treatment of Coal Refuse at HPM A Continuing Success", West Virginia Dept. of Environmental Protection Acid Mine Drainage Seminar, Clarksburg, West Virginia, Apr. 1989.

Thomas C. Means and J. Michael Klise (editors), "Symposium Issue: Acid Rock Drainage", *C & M Mining Law Monitor*, Jan. 1996.

West Virginia Surface Mine Drainage Task Force and West Virginia Mining & Reclamation Association (sponsors), "Proceedings", Seventeenth Annual West Virginia Surface Mine Drainage Task Force Symposium, Apr. 2–3, 1996.

*Primary Examiner*—David A. Simmons
*Assistant Examiner*—Betsey Morrison Hoey
*Attorney, Agent, or Firm*—Steptoe & Johnson

[57] ABSTRACT

The present invention combine an alkaline adjuvant surfactant, and water, thereby creating a treatment mixture, for eliminating acid generation in sulfide bearing material. After determining a level of acidity of a sulfide bearing material, a user derives an alkaline mixture to level the of acidity of the sulfide bearing material. The alkaline mixture of the present invention comprises highly reactive calcium oxide and lower reactive calcium carbonate. The user then combines the alkaline mixture with an adjuvant surfactant and water to generate a treatment mixture. The treatment mixture is applied to the sulfide bearing material, thereby eliminating acid generation.

15 Claims, 1 Drawing Sheet

TREATMENT OF ACID GENERATING SULFIDE BEARING MATERIAL

This application is a division of application Ser. No. 08/678,233, filed Jul. 11, 1996 now U.S. Pat. No. 5,846,279 issued Dec. 8, 1998.

BACKGROUND OF THE INVENTION

1. Field of the Invention

This invention relates to the control of acid mine drainage and acid rock drainage, and more specifically, to the treatment of sulfide bearing material with alkaline compounds combined with adjuvant surfactants and water.

2. Related Art

For years it has been known that mining or storage of sulfide bearing material (metal ores, coal seams, mine spoils, tailings, refuse, etc.) results in adverse environmental conditions, in particular, the generation of acidic waters. Acidic waters adversely affect flora and fauna and are a major environmental concern of producers, processors, regulatory agencies, and people who handle and store sulfide bearing material.

The oxidation of the mineral pyrite ($FeS_2$) and other sulfur bearing compounds produce acidic waters. The chemical reactions involve the oxidation of sulfur bearing compounds in the presence of oxygen and water forming iron hydroxide and sulfuric acid. The acidic waters are commonly called Acid Mine Drainage (AMD) or Acid Rock Drainage (ARD).

The bio-activity of oxidizing bacteria (Ferrobacillus and Thiobacillus) greatly increases the rate of pyrite oxidation. These bacteria require an acidic environment in which to survive. Because the rate of pyritic oxidation is greater in the presence of these bacterium, the rate of sulfuric acid generation also increases. Once the acid generation process is initiated, these bacteria multiply, sustaining and escalating the pyrite oxidation rate and the associated rate of sulfuric add generation. It is not uncommon to have AMD and ARD water with very low pH values of 2.1 to 3.0.

Convention methods for treating sulfide bearing material chemically treat acidic water after it has been produced, but prior to the water leaving the mining or storage area. Therefore, conventional methods treat the by-product of a sulfide bearing material, but does not directly treat the source or sulfide bearing material itself. Various alkaline compounds are used for treating acidic water, including sodium hydroxide, anhydrous ammonia, limestone, phosphate, and calcium hydroxide. These chemicals are effective in varying degrees for neutralizing acidic waters, but they are not completely effective.

One disadvantage to the conventional method pertains to the flow of the acidic water. As the flow of acidic water from the mining or storage operation varies, the application rate of the neutralizing agent must also vary; otherwise, either over or under treatment of the acidic water occurs. In either case, the water discharged is not within the required quality specification and the environment is negatively affected.

Another disadvantage is that the acidic water dissolves and mobilizes several metals, in particular, iron and manganese, which under neutral or basic conditions remain relatively insoluble. However, the metals are at elevated levels in acidic water, therefore, direct discharge is not permitted. As a result of these elevated levels, these elements must be monitored and maintained within the allowable limits as determined by the National Pollution Discharge Elimination on System (NPDES) permitting process.

A further disadvantage requires continual treatment of the acidic waters to stay within the NPDES compliance limits. During the neutralization process of raising the pH of the acidic water, iron and manganese are precipitated out of solution forming a solid which slowly settles to the bottom of the treatment basin. These chemical precipitates gradually fill the treatment basin thereby decreasing the remaining liquid volume of the basin. The decreased liquid volume reduces the retention time of the water in the treatment basin, thereby reducing the time available for solids to settle out of the water. This situation increases the risk of discharging water which is not in compliance with NPDES criteria for pH, metals, and suspended solids.

A still further disadvantage is that acidic water migrates to the lowest point in a cool system. If movement of the acidic water is not contained within an impermeable barrier (e.g. pipe, plastic, glass, etc.) the acidic waters flows into the underlying groundwater system. Once the acidic water enters the groundwater system, the detrimental affects on flora and fauna becomes widespread. Containment and treatment of the affected groundwater system is difficult, if not impossible.

A still further disadvantage of the conventional method is that the generation of acidic waters is a long term situation that, with present treatment methods, requires perpetual chemical treatment. Therefore, funding for long term treatment of acidic waters and long term responsibility and liability for environmental protection is an extreme problem. The problem is further complicated by the fact that mining and sulfide handling operators (individuals and companies) are often not perpetual entities. As a result, there are many examples of operators abandoning properties that discharge acidic water. To date, there is no known solution to this problem, rather the issue is now addressed through regulatory actions or litigation dealing with responsibility and liability for proper treatment and costs, required maintenance and monitoring personnel, cleaning and disposal of treatment pond sediments, and methodology, cost and maintenance of disposal areas. The focus of such regulatory and/or civil actions is restricted, however, by the limitation of the current methodologies for treating acidic waters (i.e. treatment of the symptom and not the source).

Therefore, there is a need for a system and method of treating acidic generating sulfide bearing material prior to acidic water being produced by the water's exposure to the sulfide bearing material.

SUMMARY OF THE INVENTION

The present invention solves the current problem of treating sulfide bearing material prior to the production of acidic water by applying a treatment mixture to the source of the acid generation. More specifically, the present invention applies a treatment mixture directly to sulfide beating material. The treatment mixture combines an alkaline based compound with an adjuvant surfactant compound and water, thereby controlling and abating acid reactions such that the sulfide bearing material does not generate acidic water. In contrast, the conventional method treats the problem of acidic water after the acid generating chemical reactions have already occurred.

The alkaline based compound of the present invention combines highly reactive calcium oxide with lower reactive calcium carbonate. The highly reactive calcium oxide immediately raises the pH of the sulfide bearing material. Thus, for example, in the sulfide bearing material pyrite, the calcium oxide eliminates all oxidating bacteria and the rapid oxidation of the pyrite. In contrast, the lower reactive calcium carbonate slowly disassociates over a long period of time, thereby providing a long term basic chemical environment. Therefore, the combination of high and low reactive calcium compounds neutralize sulfuric acid generated at the source of the sulfide bearing material.

The combination of high and low reactive calcium compounds with an adjuvant surfactant and water provides an immediate and long term solution to the problem of acid mine drainage (AMD) and acid rock drainage (ARD). The adjuvant surfactant and water enables the dispersement of the alkaline based components through the sulfide bearing material, eliminates bacteria growth, and prevents the re-inoculation by water or air borne bacteria.

Therefore, the present invention embodies this unique combination of alkaline based compounds, adjuvant surfactant and water. Although conventional methods use alkaline based compounds for treating sulfide bearing material, there is no known conventional method that combines alkaline based compounds with an adjuvant surfactant and water.

One conventional use of adjuvant surfactants is concerned with assisting in the application of chemicals for maintaining and/or rejuvenating flora and fauna. More specifically, conventional users of an adjuvant surfactant for this purpose only use a minimal amount of an adjuvant surfactant to avoid killing ground cover.

Another conventional use of adjuvant surfactants involves the use of a pelletized adjuvant surfactant for treating refuse piles. In operation, a user distributes the adjuvant surfactant pellets over the surface of the refuse pile. The user then applies water to the covered area or waits for rain water. After the water is applied, the adjuvant surfactant pellets dissolve and permeate into the refuse pile. The adjuvant surfactant pellets acts as a time release for distributing a chemical treatment throughout the refuse pile.

In contrast to these conventional uses of adjuvant surfactants, the preferred embodiment of the present invention uses an adjuvant surfactant subterraneously in combination with alkaline based compounds and water to eliminate the acid generating bacteria found in the sulfide bearing material pyrite. Therefore, the present invention incorporates a unique and unconventional use of an adjuvant surfactant.

An advantage of the present invention is that it is based on the time release concept of highly reactive and lower reactive calcium compounds coupled with adjuvant surfactant for increased dispersion and the prevention of bacterium growth and re-inoculation. Therefore, by treating sulfide bearing material with the treatment of the present invention, the formation of AMD and ARD is controlled.

Another advantage of the present invention is that it neutralizes sulfuric acid generated at the source which may occur by the slow, naturally occurring process of oxygen combining with the sulfide bearing material to form ion hydroxide and sulfuric acid. In addition, the present invention maintains an elevated pH level so that the solubility of metals remains low. Because of low solubility, the rate of metal mobilization is minimized. Therefore, the concentration of metals in discharge water from the sulfide bearing material is within acceptable environmental limits and protects the groundwater system from environmental damage.

A further advantage of the present invention is the affect on the crystal lattice of the clay minerals which may be a component of the sulfide bearing material. The high pH environment caused by the calcium oxide combining with water to form calcium hydroxide, facilitates the ionic substitution of calcium for sodium into the clay crystal structure. This ionic substitution expands the structure of the clay mineralogy, allowing the water to drain more freely from the clay substratum, thereby providing near term dewatering of the sulfide bearing material.

A still further advantage of the present invention is that over time, secondary crystal growth occurs which intertwines the particles of the sulfide bearing material. The high pH resulting from the present invention drives complex chemical reactions between calcium, alumina, and silica. These reactions foster crystal growth that causes particle intertwining of the sulfide bearing material. This intertwining reduces the permeability and porosity of the material, adding strength and mass, and retarding the flow of water through the sulfide bearing material. This affect reduces the quantity of water that can be added to the system and recharge the sulfide bearing material. With limited recharge water, the potential flushing of the alkaline mixture from the water system is reduced, the high pH environment is maintained, and the chemical reactions occur, thereby reducing and eliminating acid generation.

A still further advantage of the present invention is the elimination of long term environmental liability for producers, processors, governmental agencies and society. With the control of AMD and ARD, the water is of such a quality that treatment is not necessary to meet the environmental standards. Because perpetual treatment is no longer necessary, chemical precipitation does not occur which eliminates the need to clean and dispose of treatment basin chemical precipitates. Without the need to dispose of treatment basin chemical precipitates, a disposal site for these precipitates is not required including the environmental safeguards required for the disposal site. Therefore, the present invention reduces the long term economic liability of the producers, processors, and government agencies.

The ramifications of the present invention are many and have wide reached implications. AMD and ARD are a continuing problem for the mining industry and others who handle sulfide bearing material. Therefore, the present invention controls one of the most detrimental and environmentally sensitive problems of mining and other industries handling sulfide bearing material mixture a sound environmental manner. By applying an alkaline mixture and adjuvant surfactant according to the present invention to the source of the problem, i.e. the sulfide bearing material, the problems of AMD and ARD are eliminated. The present invention provides a safe, environmentally sound method of treating sulfide bearing material, thereby allowing industries to handle sulfide bearing material to produce needed raw materials and finished products for society. The present invention has application to sulfide metal mining, coal mining, waste disposal facilities, and other industries, including but not limited to, the power generating industry.

BRIEF DESCRIPTION OF THE FIGURES

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE PREFERRED EMBODIMENTS

Figure 1:
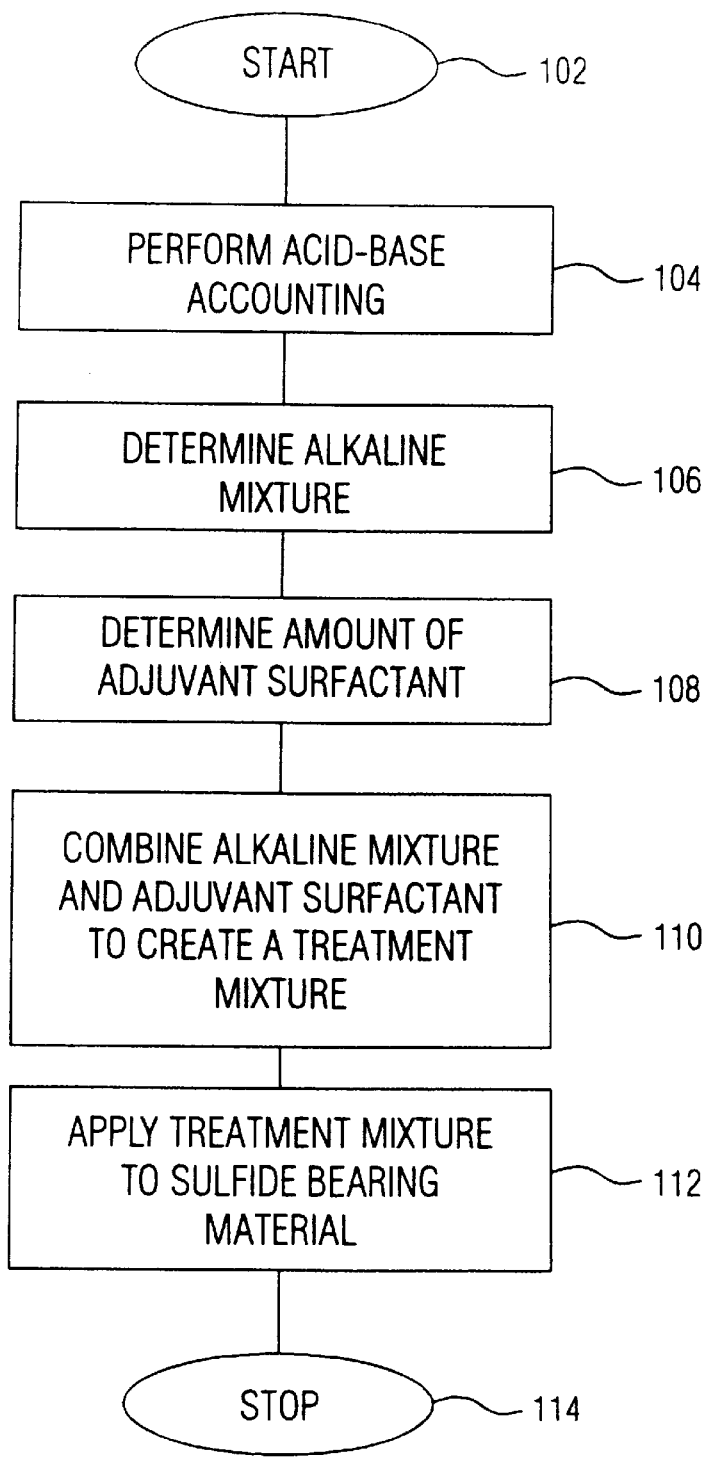
FIG. 1 is a control flow diagram illustrating the preferred embodiment of the present invention and the process of treating acid generating sulfide bearing material.

The present invention provides a technique for eliminating acid generation in sulfide bearing material. The preferred embodiment of the present invention is described in terms of the sulfide bearing material pyrite for convenience purpose only. It would be readily apparent to one of ordinary skill in the relevant art to apply the present invention to other sulfide baring materials.

a. Control flow of the present invention

FIG. 1 is a control flow diagram illustrating the treatment of acid generating sulfide being material. Processing begins at step 102 after sulfide bearing material has been located and initially proceeds to step 104. In step 104, a user of the present invention performs acid-base accounting on a target system. Results of an acid-base accounting indicate the acidity level of the target system. Acid-base accounting is well known in the relevant art. It would be readily apparent to one of ordinary skill to perform acid-base accounting on a target system.

Continuing to step 106, the user determines an alkaine mixture required to neutralize the acidity level of the target system as determined in step 104. The required alkaline mixture is based on the actual acidity level. The determination of the required composition of the alkaline mixture is well known in the relevant art. More specifically, it would be readily apparent to one of ordinary skill in the relevant art to derive an alkaline mixture for neutralizing a specific acidity level of a target system.

The preferred embodiment of an alkaline mixture comprises highly reactive calcium oxide, lower reactive calcium carbonate, or a combination thereof. The highly reactive calcium oxide provides an initial high pH that is needed to eliminate the oxidizing bacterium of pyrite and halt the rapid acid formation chemical reactions. The lower reactive calcium carbonate maintains the alkaline chemical environment, thereby keeping the slow, naturally occurring oxidation of pyrite and its sulfuric acid component under control. The calcium carbonate address the long term problems associated with acid mine drainage (AMD) and acid rock drainage (ARD). The preferred embodiment of the present invention is described in terms of calcium oxide and calcium carbonate for convenience purpose only. It would be readily apparent for one of ordinary skill to use an alkaline mixture comprising comparable alkaline components.

Continuing to step 108, the user determines an amount of adjuvant surfactant required for applying the alkaline mixture derived in step 106. The use of an adjuvant surfactant enables the alkaline mixture to be dispersed to a greater extent throughout the sulfide bearing material. Therefore, the adjuvant surfactant enhances the overall effectiveness of the alkaline mixture. The adjuvant surfactant also inhibits bacterial growth which may try to re-establish itself if additional air or water bearing bacteria is re-introduced into the target system.

Based on the facts and circumstances of the amount of sulfide bearing material requiring treatment and the required amount of the alkaine mixture for neutralizing the acidity level of the sulfide bearing material, the user determines the amount of adjuvant surfactant needed to apply the alkaline mixture. For example, in a preferred embodiment of the present invention, one application comprises 2.5 gallons of adjuvant surfactant for 3000 gallons of alkaline mixture and water. Once a person of ordinary skill in the relevant art is taught the present invention, it would be readily apparent to the person how to derive alternative proportions of adjuvant surfactant and an alkaline mixture to eliminate acid generation in sulfide bearing material.

The preferred embodiment of the adjuvant surfactant is a liquid form. A liquid adjuvant surfactant provides faster and a more equal distribution of the alkaline mixture, thereby providing a more effective treatment of the sulfide bearing material. An alternate embodiment of the adjuvant surfactant, however, is a solid form or pelletized adjuvant surfactant. Both liquid and solid forms of adjuvant surfactants are commercially available.

Continuing to step 110, the user of the present invention combines the alkaline mixture of step 106 with the adjuvant surfactant of step 108 and water, thereby creating a treatment mixture. The preferred embodiment of the present invention combines the alkaline mixture, the adjuvant surfactant, and the water prior to continuing to step 112. Alternative embodiments are discussed below. In addition, the preferred embodiment of the present invention uses manufactured water; that is, it combines the alkaline mixture and adjuvant surfactant with water from a fire hydrant, water truck, pump, or other similar source. It should be understood, however, that an alternative embodiment may use naturally occurring water such as rain water, river water, etc.

In step 112, the user applies the treatment mixture directly to the source of the acid generation; that is, the sulfide bearing material. In the preferred embodiment, the user applies the treatment mixture in a well known, conventional manner, including but not limited to, subterranean injection and surface liquid application. It would be readily apparent to one of ordinary skill in the relevant art to know how to apply the treatment mixture to a sulfide bearing material. As a result of the application, the treatment mixture prevents the sulfide bearing material from generating acidic water. This chemical process is described in greater detail below. After the treatment mixture has been applied, the user continues to step 114 and stops treatment.

In an alternative embodiment, a user may combine the alkaline mixture, the adjuvant surfactant, and the water during the application step of the present invention. More specifically, the user may first distribute only the alkaline mixture over a target area containing the sulfide bearing material. The user may then distribute the adjuvant surfactant over the target area, followed by the application of water. It would be readily apparent to one of ordinary skill in the relevant art to derive alternate techniques for applying the treatment of the present invention.

In another alternative embodiment, after the user applies the treatment mixture to the sulfide bearing material, the user may perform a second acid-base accounting of the target system. If the acidity level of the target system has not been corrected, the user may repeat the process and develop a second treatment. More specifically, the user would use the new acidity level to determine a second alkaline mixture, combine the second alkaline mixture with the adjuvant surfactant to create a second treatment mixture, and then apply the second treatment mixture to the sulfide bearing material. This process may be repeated as needed to completely neutralize the acid generating sulfide bearing material.

b. Chemical description of the present invention

Equation 1 below illustrates the creation of acid water by the sulfide bearing material pyrite.

$$2FeS_2 + 7O_2 + \text{bacteria} \rightarrow 2FeSO_4 + 2H_2SO_4 \qquad \text{equation 1}$$

In equation 1, the sulfide bearing material containing pyrite ($FeS_2$) is exposed to the atmosphere at which time oxygen ($O_2$) and bacteria begin to react with the pyrite. As water is added to the sulfide bearing material, either by natural or manmade processes, the reaction rate increases thereby turning the pH environment acidic. This provides an environment in which the bacterium can survive and multiply. The bacteria then attacks the pyrite, feeing on its iron content, and breaking the iron-sulfur chemical bond. As the bacteria reproduce and multiple, the disassociation rate of iron and sulfur increases exponentially. The liberation of sulfur and its combination with oxygen forms the sulfate radical ($SO_4$-), which in turn combines with iron and hydrogen.

Equations 2 and 3, as shown below, illustrate the continuing reaction of the recently formed iron sulfate ($FeSO_4$) and sulfuric acid ($H_2SO_4$) with oxygen ($O_2$) and water ($H_2O$) to form iron hydroxide ($Fe(OH)_2$).

$$4FeSO_4+2H_2SO_4+O_2 \rightarrow 2Fe(SO_4)_3+2H_2O \qquad \text{equation 2}$$

$$Fe_2(SO_4)_3+6H_2O \rightarrow 2Fe(OH)_3+3H_2SO_4 \qquad \text{equation 3}$$

During this process, the iron is in the ferrous state and thus is mobile in an acidic environment until it is oxidized to ferric iron. If iron is flushed from the target water system in the ferrous state, the water quality is degraded and does not meet environmental quality standards.

The neutralization of AMD and ARD is shown below in equations 4 and 5.

$$CaO+H_2O \rightarrow Ca(OH)_2 \qquad \text{equation 4}$$

$$Ca(OH)_2+H_2SO_4 \rightarrow CaSO_4+2H_2O \qquad \text{equation 5}$$

Equation 4 shows the highly reactive calcium oxide (CaO) component of a preferred embodiment of an alkaline mixture combining with water ($H_2O$) to form calcium hydroxide ($Ca(OH)_2$), a strong base. If sulfuric acid is present in the AMD or ARD water, the neutralization process of the present invention occurs as shown in equation 5. The calcium ion combines with the sulfate radical to form calcium sulfate ($CaSO_4$) and the hydrogen and oxygen combine to form water ($H_2O$). Calcium sulfate, also known as the mineral gypsum, has a low solubility over a wide range of chemical environments. Therefore, the sulfate radical will not likely dissociate from the calcium and re-mobilize. In addition, the excess of calcium hydroxide results in the environment remaining alkaline and having an elevated pH. Because the Ferrobacillus and Thiobacillus bacterium cannot survive in the alkaline environment, the major factor of rapid dissociation of pyrite is eliminated.

As shown in equation 4, the calcium hydroxide can be flushed from the sulfide bearing material, thereby reestablishing the acid generating process via the natural oxidation of the sulfide bearing material. This is a slow process in the absence of Ferrobacillus and Thiobacillus bacteria. Therefore, to prevent the re-establishment of the acid generating process, the preferred embodiment of the present invention combines a lower reactive and less soluble calcium carbonate ($CaCO_3$) component to the highly reactive calcium oxide component. Equation 6 below illustrates the dissociation of calcium carbonate in the presence of water ($H_2O$) to form a strongly basic calcium hydroxide ($Ca(OH)_2$), a weak carbonic acid ($HCO_3$), and carbon dioxide ($CO_2$).

$$CaCO_3+H_2O \rightarrow Ca(OH)_2+HCO_3+CO_2 \qquad \text{equation 6}$$

Therefore, as shown in equation 7 below, the present invention generates calcium hydroxide ($Ca(OH)_2$) over the long term to react with any sulfuric acid ($H_2SO_4$) which may be generated by the slow oxidation of the sulfide bearing material.

$$Ca(OH)_2+H_2SO_4 \rightarrow CaSO_4+H_2O \qquad \text{equation 7}$$

The reaction products of calcium hydroxide and sulfuric acid are the same as those shown in equation 5 above. That is, the reaction products are calcium sulfate (CaSO) and water ($H_2O$).

Equation 8, as shown below, illustrates the general reaction of calcium sulfate ($CaCO_3$) and iron carbonate ($FeS_2$). Both compounds occur naturally and are not detrimental to the environment. Thus, the addition of calcium carbonate to the alkaline mixture of the present invention provides long term control of AMD and ARD.

$$CaCO_3+FeS_2+H_2O \rightarrow CaSO_4+FeCO_3 \qquad \text{equation 8}$$

c. Testing of the present invention

The preferred embodiment of the present invention has been applied to the sulfide bearing material pyrite in the following quantities. In one application, the alkaline mixture comprised 7 tons of calcium oxide ad 2500 gallons of water. The alkaline mixture was combined with 2.5 gallons of liquid adjuvant surfactant to create the treatment mixture. The treatment mixture was applied to the pyrite. The treatment resulted in the elimination of all acid generating bacteria located in the pyrite; thereby resulting in the elimination of acid water.

In an alternative application, the alkaline mixture comprised 7 tons of lime with 3000 gallons of water. The alkaline mixture was then combined with 1 gallon of liquid adjuvant surfactant to create the treatment mixture. After applying the treatment mixture to the pyrite, all acid generating bacteria were eliminated.

Conclusion

While various embodiments of the present invention have been described above, it should be understood that they have been presented by the way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined in accordance with the following claims and their equivalents.

What is claimed is:

1. A treatment mixture for eliminating acid generation by killing bacteria found in solid, inorganic sulfide bearing material, comprising:

(a) a highly reactive alkaline component that generates an initial pH to kill the bacteria and neutralize a level of acidity of the solid, inorganic sulfide bearing material;

(b) a lower reactive alkaline component that generates a lower maintenance pH to provide a long term alkaline environment in the solid, inorganic sulfide bearing material after the bacteria is eliminated; and (c) an adjuvant surfactant that acts as a dispersing agent for dispersing said highly reactive alkaline component and said lower reactive alkaline component to the solid, inorganic sulfide bearing material, wherein said adjuvant surfactant is less than about 0.1% of the total weight of the treatment mixture.

2. The treatment mixture of claim 1, further comprising water wherein said highly reactive alkaline component and said lower reactive alkaline component are about 40% of the total weight of the treatment mixture.

3. The treatment mixture of claim 1, wherein said highly reactive alkaline component generates an initial pH of at least about 12 for killing the bacteria found in the sulfide bearing material and said lower reactive alkaline component provides a lower maintenance pH between about 7 and 9 for maintaining the long term alkaline environment in the sulfide bearing material after the bacteria is eliminated.

4. The treatment mixture of claim 1, wherein said highly reactive alkaline component is selected from the group of calcium oxide, calcium carbonate, calcium hydroxide, magnesium oxide, magnesium carbonate, magnesium hydroxide, soda ash, lime, sodium hydroxide, and ammonium hydroxide.

5. The treatment mixture of claim 1, wherein said adjuvant surfactant is in a liquid form.

6. The treatment mixture of claim 1, wherein said adjuvant surfactant is in a solid form.

7. The treatment mixture of claim 1, wherein said highly reactive alkaline component is selected from the group of calcium oxide, calcium hydroxide, magnesium oxide, magnesium hydroxide, soda ash, lime, sodium hydroxide, and ammonium hydroxide, and said lower reactive alkaline component is selected from the group of calcium carbonate, and magnesium carbonate.

8. The treatment mixture according to claim 1, wherein said highly reactive alkaline component generates an initial pH of at least about 12 for killing the bacteria found in the sulfide bearing material and said lower reactive alkaline component provides a lower maintenance pH between about 7 and 9 for maintaining the long term alkaline environment in the sulfide bearing material after the bacteria is eliminated.

9. The treatment mixture of claim 1, wherein said lower reactive alkaline component is selected from the group of calcium carbonate, and magnesium carbonate.

10. A treatment mixture for eliminating acid generation by killing bacteria found in solid, inorganic sulfide bearing material, comprising:

an alkaline mixture comprising a highly reactive alkaline component that generates an initial pH to kill the bacteria and neutralize a level of acidity of the solid, inorganic sulfide bearing material and a lower reactive alkaline component that generates a lower maintenance pH to provide a long term alkaline environment in the solid, inorganic sulfide bearing material after the bacteria is eliminated, wherein said highly reactive alkaline component is calcium oxide and said lower reactive alkaline component is calcium carbonate; and an adjuvant surfactant that acts as a dispersing agent for dispersing said alkaline mixture to the solid, inorganic sulfide bearing material;

wherein said alkaline mixture is about 99% of the total weight of the treatment mixture.

11. The treatment mixture of claim 10, further comprising water wherein said alkaline mixture is about 40% of the total weight of the treatment mixture.

12. The treatment mixture of claim 10, wherein said adjuvant surfactant is in a liquid form.

13. The treatment mixture of claim 10, wherein said adjuvant surfactant is in a solid form.

14. A treatment mixture for eliminating acid generation by killing bacteria found in solid, inorganic sulfide bearing material, comprising:

(a) about 7 tons of calcium oxide that provides an initial pH of at least 12 to kill the bacteria and neutralize a level of acidity of the solid, inorganic sulfide bearing material and that generates a lower maintenance pH to provide a long term alkaline environment in the solid, inorganic sulfide bearing material after the bacteria is eliminated; and (b) about 1 gallon of a liquid adjuvant surfactant that acts as a dispersing agent for dispersing said calcium oxide to the solid, inorganic sulfide bearing material.

15. The treatment mixture of claim 14, further comprising about 3000 gallons of water.

* * * * *